United States Patent [19]

Osman

[11] 4,368,135
[45] Jan. 11, 1983

[54] ANISOTROPIC COMPOUNDS WITH NEGATIVE OR POSITIVE DC-ANISOTROPY AND LOW OPTICAL ANISOTROPY

[75] Inventor: Maged A. Osman, Zurich, Switzerland

[73] Assignee: BBC, Brown, Boveri & Company, Ltd., Baden, Switzerland

[21] Appl. No.: 164,692

[22] Filed: Jun. 30, 1980

[30] Foreign Application Priority Data

Jul. 18, 1979 [CH] Switzerland .................. 6671/79

[51] Int. Cl.$^3$ .................. C09K 3/34; C07C 121/75
[52] U.S. Cl. .................. 252/299.63; 252/299.5; 260/465 D; 260/465 R; 260/465 G; 260/465 H; 260/465 F; 560/1; 560/20; 560/21; 560/23; 560/59; 560/61; 560/62; 560/64; 560/65; 560/73; 560/102; 560/106; 560/107; 560/118; 560/126; 568/585; 568/631; 568/642; 568/648; 568/649; 568/656; 568/659; 568/661; 570/129; 570/182
[58] Field of Search .......... 252/299.5, 299.63, 299.64, 252/299.65, 299.66, 299.67; 260/465 D, 465 H, 465 R, 465 GF; 560/1, 20, 21, 23, 59, 61, 62, 65, 64, 73, 102, 106, 107, 118, 125; 568/585, 642, 649, 648, 631, 656, 659, 661; 570/129, 182

[56] References Cited

U.S. PATENT DOCUMENTS

| | | | |
|---|---|---|---|
| 4,009,934 | 3/1977 | Goodwin et al. | 252/299.62 |
| 4,113,647 | 9/1978 | Coates et al. | 252/299.63 |
| 4,148,130 | 4/1980 | Doller et al. | 252/299.5 |
| 4,154,697 | 5/1979 | Eidenschink et al. | 252/299.63 |
| 4,222,887 | 9/1980 | Matsufusi | 252/299.5 |
| 4,229,015 | 10/1980 | Krause et al. | 252/299.63 |
| 4,237,026 | 12/1980 | Eidenschink et al. | 252/299.63 |
| 4,256,656 | 3/1981 | Beguin et al. | 252/299.67 |
| 4,279,770 | 7/1981 | Inuaki et al. | 252/299.63 |
| 4,290,905 | 9/1981 | Kanbe | 252/299.63 |

FOREIGN PATENT DOCUMENTS

| | | | |
|---|---|---|---|
| 2752975 | 8/1978 | Fed. Rep. of Germany | 252/299.63 |
| 2854010 | 6/1979 | Fed. Rep. of Germany | 252/299.63 |
| 55-29545 | 3/1980 | Japan | 252/299.64 |
| 56-43386 | 4/1981 | Japan | 252/299.63 |
| 105701 | 5/1974 | German Democratic Rep. | 252/299.63 |
| 2039937 | 8/1980 | United Kingdom | 252/299.66 |
| 2061311 | 5/1981 | United Kingdom | 252/299.57 |
| 2063287 | 6/1981 | United Kingdom | 252/299.60 |

OTHER PUBLICATIONS

Dewar, M. J. S., et al.; JACS, vol. 92, No. 6, pp. 1582-1586 (1970).
Demus, D., et al., Mol. Cryst. Liq. Cryst., vol. 63, pp. 129-144 (1981).
Gray, C. W., et al.; Mol. Cryst. Liq. Cryst., vol. 67, No. 1-4, pp. 1-24 (1981).

*Primary Examiner*—Teddy S. Gron
*Attorney, Agent, or Firm*—Oblon, Fisher, Spivak, McClelland & Maier

[57] ABSTRACT

Anisotropic compounds with negative or positive DCA and $\Delta n \leq 0.2$ have the formula (1)

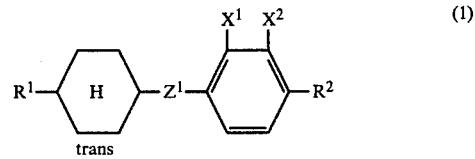

in which $R^1$ and $R^{2\ 1}$ *are independently hydrogen, alkyl, alkoxy having 1 to 12 carbon atoms respectively, or one of* $R^1$ and $R^2$ can represent cyclical fragment of formulae (1a) or (1b);

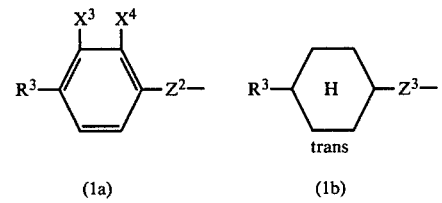

the bridges $Z^1$, $Z^2$ and $Z^3$ are identical or different and means covalent bonds or carboxyl or oxycarbonyl groups; $R^3$ is hydrogen, alkyl or alkoxy group having 1 to 12 carbon atoms, respectively; $X^1$ and $X^4$ are independently hydrogen, halogen, nitrile or nitro, wherein at least one of $X^1$ and $X^4$ is not hydrogen when $R^2$ represents a cyclical fragment of formula (1a) or (1b) and $Z^2$ is a carboxyl group or $Z^3$ is an oxycarbonyl group, respectively. Liquid crystal compositions are also disclosed.

15 Claims, No Drawings

ANISOTROPIC COMPOUNDS WITH NEGATIVE OR POSITIVE DC-ANISOTROPY AND LOW OPTICAL ANISOTROPY

BACKGROUND OF THE INVENTION

1. Field of the Invention

The invention relates to new anisotropic compounds with negative or positive dielectric constant anisotropy and low, e.g., 0.2 optical anisotropy ($\Delta n$) at the most, as well as liquid crystal (LC) compositions containing these anisotropic compounds and are used as the dielectric for liquid crystal indicators.

2. Description of the Prior Art

The anisotropic compounds known up till now for liquid crystal compositions whose dielectric constant-anisotropy, abbreviated DCA or $\Delta\epsilon$, is negative, are mostly of two or three combinations, made up of aromatic rings with one of two carboxyl groups and, if necessary, a covalent bond as a bridge between the rings, and with one or more side groups, i.e., core substituent groups not lying in the molecular longitudinal axis, such as nitrile or nitro groups, particularly, such as described in German AS No. 2 240 864, German Os Nos. 2 613 293, 2 835 662 and 2 836 086. These known anisotropic compounds with negative DCA ($\Delta\epsilon$), however, have high viscosity values as well as high values for optical anisotropy ($\Delta n$) ($\Delta\epsilon = \epsilon_{11} - \epsilon_{\perp}$ and $\Delta n = n_{11} - n_{\perp}$). The DCA of a compound is negative if the dielectric constant ($\epsilon$) parallel to the molecular axis is smaller than the dielectric constant perpendicular to the molecular axis. The optical anisotropy ($\Delta n$) of a compound is positive if its refraction index ($n_{195}$) perpendicular to the molecular axis is smaller than its refraction index ($n_{11}$) parallel to the molecular axis; this optical anisotropy value, i.e., $\Delta n = n_{11} - n_{\perp}$ is designated "low" here if it is smaller than, or at the most 0.2 ($\Delta n \leq 0.2$). Suitable methods for measuring $\Delta n$ are known in the literature (e.g., I. Haller et al, *Mol. Cryst. and Liqu. Cryst.* 16/1972/53–59) and usually refer to a definite light wave length (here 633 nm).

It is known from the literature, e.g., German OS No. 2 636 684, that the viscosity of liquid crystalline and linear aromatic compounds with no side groups, such as biphenyl nitriles, can be reduced by substituting a cyclohexane ring for one of the phenylene rings. This possibility for producing anisotropic compounds with high negative DC-anisotropy and low $\Delta n$-values suited for LC compositions has remained unused until now. To be sure such compounds with a side group, e.g., methyl or ethyl groups or chlorine atoms, were mentioned in the German OS No. 2 752 975 among a number of specially described, linear, tri-cyclic diesters with one or two benzol-ring(s) and two or one cyclohexane ring(s); although mention was made of the possibility of a side nitrile group, it was not recognized that a new group of advantageous anisotropic compounds with negative, not to mention strongly negative, DC-anisotropy would have been made accessible according to the structural principle disclosed there.

Anisotropy, i.e., enantiotropic liquid crystalline or nonotropic or potentially liquid crystalline compounds with high negative DC-anisotropy and low $\Delta n$-values are required for LC-indicators, as was described by the applicant in the German PA No. 35 863.6, which utilize the so-called "inverse Guest-Host-effect"; furthermore, anisotropic compounds with such characteristics are also required for certain types of dynamic (scatter/leakage) cells. However, prior known anisotropic compounds with negative DC anisotropy do not satisfy the required conditions or at least not to a satisfactory degree.

A need therefore continues to exist for new anisotropic compounds with negative DCA and low optical anisotropy ($\Delta n$), e.g., for LC-indicators with multiplex operation.

SUMMARY OF THE INVENTION

Accordingly, one object of the invention is to provide anisotropic compounds with negative or positive DCA and low optical anisotropy.

A further object of the invention is to provide liquid crystal compositions comprising at least one anisotropic compound with negative or positive DCA and low optical anisotropy.

Briefly, these objects and other objects of the invention as hereinafter will become more readily apparent can be attained by providing an anisotropic compound of formula (I):

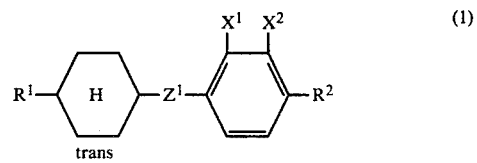

in which the side groups $R^1$ and $R^2$ are hydrogen, $C_1-C_{12}$-alkyl groups or $C_1-C_{12}$-alkoxy groups and one of the groups $R^1$ and $R^2$ can represent in addition a cyclical fragment of formula (1a) or (1b);

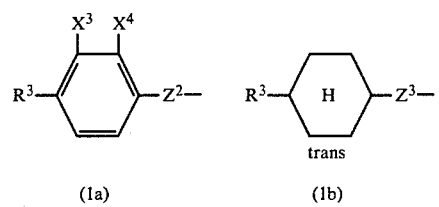

(1a)  (1b)

the bridges $Z^1$, $Z^2$ and $Z^3$ are identical or different and are simple covalent bonds or carboxyl or oxycarbonyl groups; $R^3$ is hydrogen, $C_1-C_{12}$-alkyl or $C_1-C_{12}$ alkoxy; at least one of $X^1$ to $X^4$ and preferably two or more are halogen, nitrile (preferably) or nitro, the remainder being hydrogen. At most one of $Z1$, $Z2$ and $Z3$ is carboxyl or oxycarbonyl with the proviso (A) that at least two of $X^1$ and $X^4$ are not hydrogen when $X^1$ is nitrile and $R^1$ is a cyclical fragment of formula (1a), (B) at least two of $X^1$ to $X^4$ are not hydrogen when $X^4$ is nitrile and $R^2$ is a cyclical fragment of formula (1a), and (C) that no benzene ring is directly linked to two oxygen atoms.

DETAILED DESCRIPTION OF THE PREFERRED EMBODIMENTS

This invention is directed to anisotropic compounds of the formula (1):

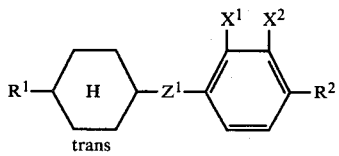

(1)

in which the side groups $R^1$ and $R^2$ are hydrogen, $C_1$–$C_{12}$-alkyl groups or $C_1$–$C_{12}$-alkoxy groups and one of the groups $R^1$ and $R^2$ can represent in addition a cyclical fragment of formula (1a9 or (1b);

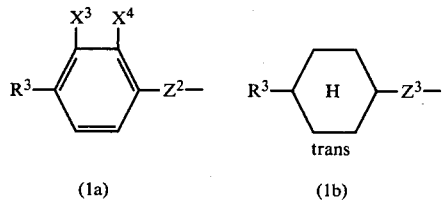

(1a)        (1b)

the bridges $Z^1$, $Z^2$ and $Z^3$ are identical or different and are simple covalent bonds or carboxyl or oxycarbonyl groups; $R^3$ is hydrogen, $C_1$–$C_{12}$-alkyl or $C_1$–$C_{12}$ alkoxy; at least one of $X^1$ to $X^4$ and preferably two or more are halogen, nitrile (preferably) or nitro, the remainder being hydrogen. At most one of Z1, Z2 and Z3 is carboxyl or oxycarboxyl with the proviso (A) that at least two of $X^1$ and $X^4$ are not hydrogen when X1 is nitrile and $R^1$ is a cyclical fragment of formula (1a), (B) at least two of $X^1$ to $X^4$ are not hydrogen when $X^4$ is nitrile and $R^2$ is a cyclical fragment of formula (1a), and (C) that no benzene ring is directly linked to two oxygen atoms.

Chlorine is particularly preferred as a halogen, although other halogens (F, Br, I) are acceptable.

It is not necessary that all of $X^1$ to $X^4$ positions be substituted; thus, up to three of the groups $X^1$ to $X^4$, preferably up to two of the groups $X^1$ to $X^4$ must be halogen, nitro or nitrile (preferably), the remainder being hydrogen.

The compounds of formula (1) as in the invention are hereinbelow designated as "compounds (1)" for the sake of brevity.

Preferred groups of the "compounds (1)" correspond to the following formulae (2) through (6):

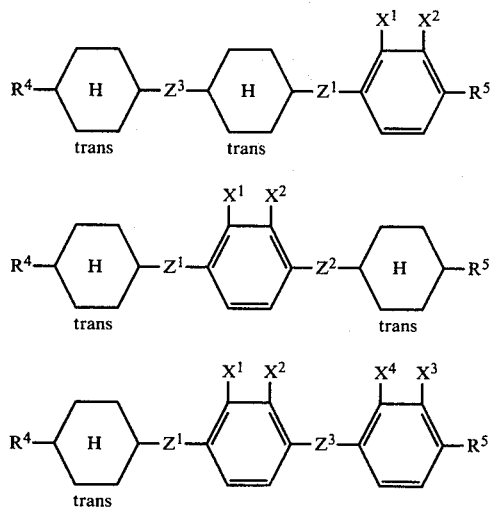

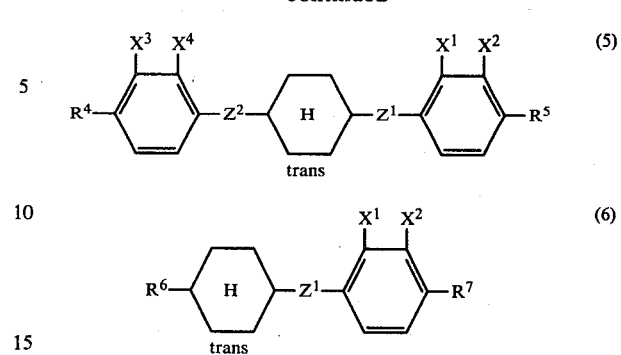

In the formulae above (2) through (6):

$R^4$ and $R^5$ are independently selected from hydrogen, $C_1$–$C_{12}$-alkyl or $C_1$–$C_{12}$-alkoxy.

$R^6$ and $R^7$ are independently selected from $C_1$–$C_{12}$-alkyl or $C_1$–$C_{12}$-alkoxy.

In all formulae (2) through (6), at least two of the groups $X^1$ to $X^4$ are preferably halogen (preferably chlorine), nitro or nitrile, with nitrile groups especially preferred. According to another preferred embodiment one of the benzol rings of the compounds of formulae (2) through (6) carries two halogen atoms, nitro groups or (preferably) nitrile groups.

It is also preferable in the formulae (2) through (5) that one of the bridges, $Z^1$, $Z^2$, $Z^3$ in each formula be carboxyl (—COO—) or oxycarbonyl (—OOC—) and the other one be a simple covalent bond.

There is at most one carboxyl or oxycarbonyl bridge in the molecule.

The "compounds (1)" can be obtained by known methods, for example, by condensation of corresponding phenols or cyclohexanols with the corresponding benzoic acids or cyclohexane carbon acid combinations. Where the respective acid components are used, preferably in the form of a corresponding reactive functional acid derivative, e.g., an acid halide, particularly the acid chloride, the reaction is carried out in a fluid organic base, such as, pyridine.

LC-compositions according to the invention contain as components a "compound (1)", e.g., in weight percentage proportions of 1–40, or several varying "compounds (1)" in even larger proportions if desired. LC-compositions are preferred which contain as components at least one compound of the formulae (2) through (6) above.

Having generally described this invention, a further understanding can be obtained by reference to certain specific examples which are provided herein for purposes of illustration only and are not intended to be limiting unless otherwise specified.

EXAMPLE 1

Production of 2-cyano-4-n-butylphenyl-(4''-n-pentyl-trans-cyclohexyl-4'-trans-cyclohexanoate (Formulae 2: $R^4$=n—$C_5H_{11}$—, $Z^3$=—, $Z^1$=—COO—, $X^1$=—CN, $R^5$=n—$C_4H_9$—). 4-trans-(4'-trans-n-pentylcyclohexyl)-cyclohexane carbon acid (7 g, 25 mM) was heated with thionylchloride (40 ml) for 30 minutes at backflow temperature. The resulting acid chloride was separated from the supernatant thionyl chloride. The acid chloride thus obtained was then trickled into a solution of 2-cyano-4-n-butylphenol (4.5 g, 25 mM) in 100 ml of pyridine at 0° C. After the reaction was finished the mixture was poured into supernatant thinned hydrochloric acid and extracted with methylene chloride. The raw product obtained from the extract by boiling it down was recrystallized from hexane. The target combination of this example obtained in this manner is nematic-enantiotrope ($T_m = 66.1°$ C., $T_c = 157.8°$ C.) and has a negative DC-anisotropy as well as a $\Delta n \leq 0.2$.

EXAMPLE 2

Production of
2,3-dichloro-4-n-pentylphenyl-(4″-n-pentyl-transcyclohexyl-4′)-trans-cyclohexanoate (Formula 2: $R^4 = n-C_5H_{11}$, $Z^3 = -$, $Z^1 = -COO-$, $X^1 = Cl$, $X^2 = Cl$, $R^5 = n-C_5H_{11}$). 4-trans-(4′-trans-n-pentylcyclohexyl)-cyclohexane carbon acid (10 g, 36.5 mM) was boiled under reflux with thionylchloride (50 ml) for one hour. The supernatant thionylchloride was distilled. The resulting acid chloride was trickled into a solution of 5.3 g (36.5 mM) of 2,3-dichloro-4-n-pentylphenol (6p 85° C./0.007 torr) in 100 ml of pyridine. The reaction mixture was stirred over night and then poured onto thinned hydrochloric acid. The product was extracted with methylene chloride. To purify it the product was recrystallized from hexane. It shows an enantiotropic nematic phase (Tm = 40° C., Tc = 180° C.) and has a negative DC-anisotropy as well as a $\Delta n \leq 0.2$.

Example 3

Production of
2,3-dicyano-4-n-pentylphenyl-(4″-n-pentyl-trans-cyclohexyl-4′)-trans-cyclohexanonate (Formula 2: $R^4 = n-C_5H_{11}$, $Z^3 = -$, $Z^1 = -COO-$, $X^1 = CN$, $X^2 = CN$, $R^5 = n-C_5H_{11}$).

According to the procedure described in Example 2, the compound of the present example was produced in an analogous manner from equimolar (36.5 mM) amounts of cyclohexane carbon acid compound of Example 2—again by converting the same with thionylchloride into the corresponding acid chloride—and, 2,3-dicyano-4-n-pentylphenol (instead of the corresponding dichlorophenol of Example 2), and worked up in the same manner as above. The compound thus obtained is also nematic-enantiotropic and hs a negative DC-anisotropy as well as a $\Delta n \leq 0.2$.

EXAMPLES 4–20

The following anisotropic "compounds (1)" also having a negative DC-anisotropy according to the invention were produced in a manner similar to that above. The cyclohexyl rings are respectively in trans-configuration: $\Delta n \leq 0.2$.

EXAMPLE

4: 2,3-dicyano-4-propylphenyl-(4″-propyl-p-phenylene-4′)-cyclohexanoate.
5: 2,3-dicyano-4-propylphenyl-(4″-pentyl-p-phenylene-4′)-cyclohexanoate.
6: 2,3-dicyano-4-propylphenyl-(2″,3″-dicyano-4″-propyl-p-phenylene-4″)-cyclohexanoate.
7: 2,3-dicyano-4-propylphenyl-(3″-cyano-4″-propyl-p-phenylene-4′)-cyclohexanoate.
8: 2,3-dichloro-4-pentylphenyl-(4″-propyl-p-phenylene-4′)-cyclohexanoate.
9: 2,3-dichloro-4-pentylphenyl-(3″-cyano-4″-propyl-p-phenylene-4′)-cyclohexanoate.
10: 2,3-dicyano-44″-pentylcyclohexyl-4′)-cyclohexanoate.
11: 2,3-dicyano-4-pentylphenyl-(4″-pentylcyclohexyl-4′)-cyclohexanoate.
12: 2,3-dichloro-4-propylphenyl-(4″-pentylcyclohexyl-4′)-cyclohexanoate.
13: 2-cyano-4-propylphenyl-(4″-pentylcyclohexyl-4′)-cyclohexanoate.
14: 2-cyano-4-pentylphenyl-(4″-pentylcyclohexyl-4′)-cyclohexanoate.
15: 2-chloro-4-pentylphenyl-(4″-pentylcyclohexyl-4′)-cyclohexanoate.
16: 2-nitro-4-pentylphenyl-(4″-pentylcyclohexyl-4′)-cyclohexanoate.
17: 2-cyano-4-propylphenyl-(4″-pentylcyclohexyl-4′)-2′-cyanobenzoate.
18: 2-cyano-4-propylphenyl-(4″-pentylcyclohexyl-4′)-3′-cyanobenzoate
19: 2-cyano-4-propylphenyl-(2″-cyano-4″-pentylphenylene-4′)-cyclohexanoate.
20: 2-cyano-4-propylphenyl-(3″-cyano-4″-pentylphenylene-4′)-cyclohexanoate.

EXAMPLES 21–38

The following compounds of formula (6) above according to the invention are anisotropic and show a negative DC-anisotropy and a $\Delta n \leq 0.2$.

EXAMPLE

21: 4-propylcyclohexyl-4′-propyl-2′,3′-dicyanobenzoate.
22: 4-propylcyclohexyl-4′-pentyl-2′,3′-dicyanobenzoate.
23: 2,3-dicyano-4-propylphenyl-4′-heptycyclohexanoate.
24: 2,3-dicyano-4-pentylphenyl-4′-propylcyclohexanoate.
25: 2,3-dicyano-4-pentylphenyl-4′-pentylcyclohexanoate.
26: 2,3-dichloro-4-propylphenyl-4′-propyloxycyclohexanoate.
27: 2,3-dibromo-4-pentylphenyl-4′-propoxycyclohexanoate.
28: 2,3-dinitro-4-pentylphenyl-4′-pentyloxycyclohexanoate.
29: 2,3-dicyano-4-propylphenyl-4′-propylcyclohexane.
30: 2,3-dicyano-4-propylphenyl-4′-pentylcyclohexane.
31: 2,3-dicyano-4-propylphenyl-4′-heptylcyclohexane.
32: 2,3-dicyano-4-pentyloxyphenyl-4′-propoxycyclohexane.
33: 2,3-dicyano-4-pentyloxyphenyl-4′-pentyloxycyclohexane.
34: 2,3-dicyano-4-propylphenyl-4′-butoxycyclohexane.
35: 2,3-dichloro-4-pentylphenyl-4′-propylcyclohexane.
36: 2,3-dinitro-4-heptylphenyl-4′-propylcyclohexane.
37: 2,3-dichloro-4-pentylphenyl-4′-butoxycyclohexane.
38: 2,3-dinitro-4-pentylphenyl-4′-butoxycyclohexane.

All compounds of Examples 1 to 38 also have advantageously low $\Delta n < 0.2$ and the cyclohexane rings are respectively in trans-configuration. The compounds (1) according to the invention have the surprising, additional advantage that their $\gamma$-values ($\gamma = (\Delta\epsilon/\epsilon)$) are small and often amount to about 2 at the most, i.e., $\gamma \leq 2$.

Having now fully described this invention, it will be apparent to one of ordinary skill in the art that many changes and modifications can be made thereto without departing from the spirit or scope of the invention set forth herein.

What is claimed as new and intended to be covered by Letters Patent is:

1. An anisotropic compound with negative or positive DC-anisotropy and an optical anisotropy $\Delta n \leqq 0.2$ having the formula (1):

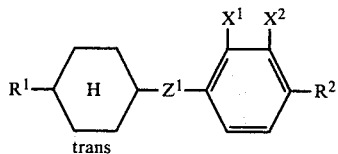
(1)

in which $R^1$ and $R^2$ are independently hydrogen, alkyl having 1 to 12 carbon atoms, alkoxy having 1 to 12 carbon atoms or one of $R^1$ and $R^2$ can represent a cyclical fragment of formulae (1a) or (1b):

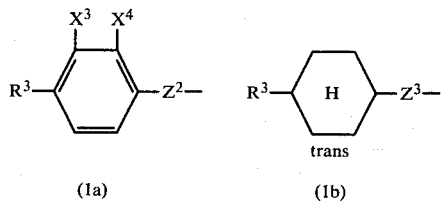

wherein one of the bridges $Z^1$, $Z^2$ and $Z^3$ in each formula is carboxyl or oxycarbonyl and the other, when present, is a covalent bond, $R^3$ is hydrogen, alkyl of 1 to 12 carbon atoms or alkoxy of 1 to 12 carbon atoms, and $X^1$ and $X^4$ are independently hydrogen, halogen, nitrile or nitro, wherein at least two of $X^1$ to $X^4$ are not hydrogen.

2. The compound of claim 1, having the formula (2):

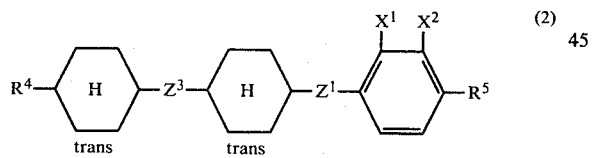
(2)

wherein $R^4$ and $R^5$ are hydrogen, alkyl or alkoxy groups having 1 to 12 carbon atoms, respectively.

3. The compound of claim 1, having the formula (3):

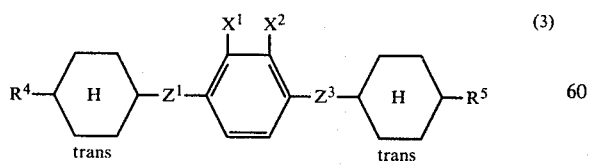
(3)

wherein $R^4$ and $R^5$ are hydrogen, alkyl or alkoxy groups having 1 to 12 carbon atoms, respectively.

4. The compound of claim 1, having the formula (4):

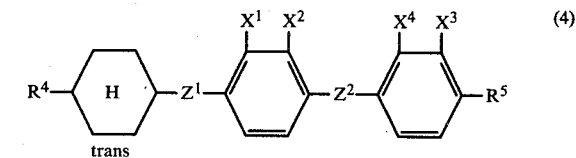
(4)

wherein $R^4$ and $R^5$ are hydrogen, alkyl or alkoxy groups having 1 to 12 carbon atoms, respectively.

5. The compound of claim 1, having the formula (5):

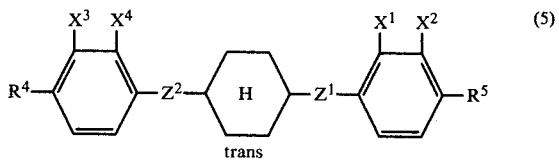
(5)

wherein $R^4$ and $R^5$ are hydrogen, alkyl or alkoxy groups having 1 to 12 carbon atoms, respectively.

6. The compound of claim 1, having the formula (6):

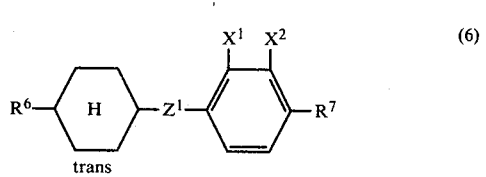
(6)

wherein $R^6$ and $R^7$ are alkyl or alkoxy groups having 1 to 12 carbon atoms, respectively.

7. The compound of claim 1, 2, 3, 4, 5 or 6, wherein both $X^1$ and $X^2$ are halogen, nitro or nitrile.

8. A liquid crystal composition which comprises at least two components at least one of which is an anisotropic compound with negative or positive DC-anisotropy and an optical anisotropy $\Delta n \leqq 0.2$, having the formula (1):

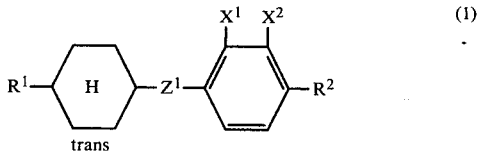
(1)

in which $R^1$ and $R^2$ are independently hydrogen, alkyl having 1 to 12 carbon atoms, alkoxy having 1 to 12 carbon atoms or one of $R^1$ and $R^2$ can represent a cyclical fragment of formula (1a) or (1b):

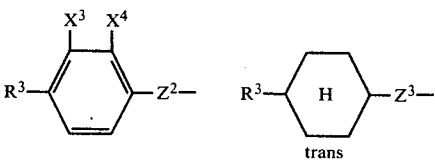

wherein one of the bridges $Z^1$, $Z^2$ and $Z^3$ in each formula is carboxyl or oxycarbonyl and the other, when present, is a covalent bond, $R^3$ is hydrogen, alkyl of 1 to 12 carbon atoms or alkoxy of 1 to 12 carbon atoms, and $X^1$ to $X^4$ are independently hydrogen, halogenn, nitrile or nitro, wherein at least two of $X^1$ to $X^4$ are not hydrogen.

9. The liquid crystal composition of claim 8, wherein the anisotropic compound has the formula (2):

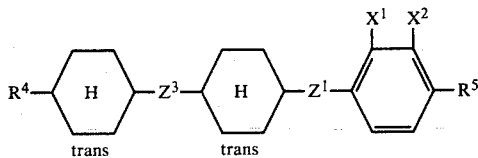

(2)

wherein $R^4$ and $R^5$ are hydrogen, alkyl or alkoxy groups having 1 to 12 carbon atoms, respectively.

10. The liquid crystal composition of claim 8, wherein the anisotropic compound has the formula (3):

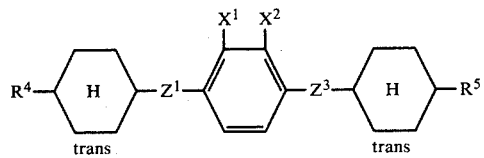

(3)

wherein $R^4$ and $R^5$ are hydrogen, alkyl or alkoxy groups having 1 to 12 carbon atoms, respectively.

11. The liquid crystal composition of claim 8, wherein the anisotropic compound has the formula (4):

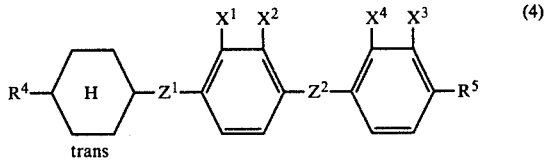

(4)

wherein $R^4$ and $R^5$ are hydrogen, alkyl or alkoxy groups having 1 to 12 carbon atoms, respectively.

12. The liquid crystal composition of claim 8, wherein the anisotropic compound has the formula (5):

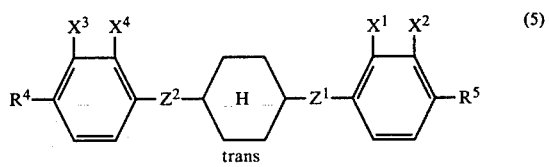

(5)

wherein $R^4$ and $R^5$ are hydrogen, alkyl or alkoxy groups having 1 to 12 carbon atoms, respectively.

13. The liquid crystal composition of claim 8, wherein the anisotropic compound has the formula (6):

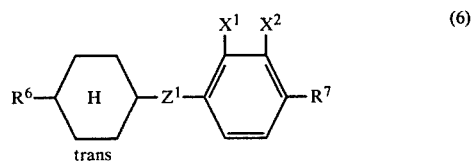

(6)

wherein $R^6$ and $R^7$ are alkyl or alkoxy having 1 to 12 carbon atoms, respectively.

14. The liquid crystal composition of claim 8, 9, 10, 11, 12 or 13, wherein both $X^1$ and $X^2$ are halogen, nitro or nirile.

15. The compound of claim 1, 2, 3, 4 or 5 where each of $R^1, R^2, R^3, R^4$, and $R^5$ when present in the compound is alkyl having 1 to 12 carbon atoms.

* * * * *